United States Patent
Muth et al.

(10) Patent No.: US 7,390,553 B2
(45) Date of Patent: Jun. 24, 2008

(54) PERFORATED LAMINATE

(75) Inventors: Mathias Muth, Wiesbaden (DE); Joachim Bauer, Seuzach (CH); Henning Roettger, Braunschweig (DE)

(73) Assignee: Fiberweb Corovin GmbH, Peine (DE)

( * ) Notice: Subject to any disclaimer, the term of this patent is extended or adjusted under 35 U.S.C. 154(b) by 227 days.

(21) Appl. No.: 10/481,940

(22) PCT Filed: Jul. 3, 2002

(86) PCT No.: PCT/EP02/07328

§ 371 (c)(1), (2), (4) Date: Jun. 9, 2004

(87) PCT Pub. No.: WO03/004259

PCT Pub. Date: Jan. 16, 2003

(65) Prior Publication Data

US 2004/0209067 A1    Oct. 21, 2004

(30) Foreign Application Priority Data

Jul. 3, 2001    (DE) ............................. 201 21 445 U

(51) Int. Cl.
*B32B 3/24*    (2006.01)
(52) U.S. Cl. ...................................... 428/132
(58) Field of Classification Search ................. 428/132
See application file for complete search history.

(56) References Cited

U.S. PATENT DOCUMENTS

| | | | |
|---|---|---|---|
| 4,280,978 A | 7/1981 | Dannheim et al. | |
| 4,610,189 A | 9/1986 | Lombardo | |
| 4,614,679 A | 9/1986 | Farrington, Jr. et al. | |
| 4,758,297 A | 7/1988 | Calligarich | |
| 4,818,586 A * | 4/1989 | Smith et al. | 428/198 |
| 5,429,854 A | 7/1995 | Currie et al. | |
| 5,830,555 A | 11/1998 | Srinivasan et al. | |
| 6,025,050 A | 2/2000 | Srinivasan et al. | |
| 6,274,218 B1 * | 8/2001 | Shimizu | 428/137 |
| 6,475,600 B1 * | 11/2002 | Morman et al. | 428/152 |

FOREIGN PATENT DOCUMENTS

| | | |
|---|---|---|
| DE | 198 56 223 A | 6/2000 |
| EP | 0 472 992 B1 | 3/1992 |
| FR | 827950 A | 5/1938 |
| GB | 2 267 680 A | 12/1993 |
| JP | 58 090916 A | 5/1983 |
| JP | 06-2 80 150 A | 10/1994 |
| WO | WO 96/40513 A | 12/1996 |
| WO | WO 98/58109 A | 12/1998 |
| WO | WO 99/65 673 A1 | 12/1999 |

* cited by examiner

*Primary Examiner*—William P Watkins, III
(74) *Attorney, Agent, or Firm*—Alston & Bird LLP

(57) ABSTRACT

The present invention relates to a perforated thermoplastic structure comprising at least a first layer (8) and a plurality of perforations, which extend through the first layer (8). The perforations have a three-dimensional, preferably approximately conical or cylindrical shape (18). A second layer forms an inner surface (20) of the shape (18), whereas the first layer forms an outer surface (21) of the shape (18). The first layer contains a thermoplastic material, whose melting point is lower than a melting point of the thermoplastic material of the second layer.

3 Claims, 3 Drawing Sheets

Figure 3
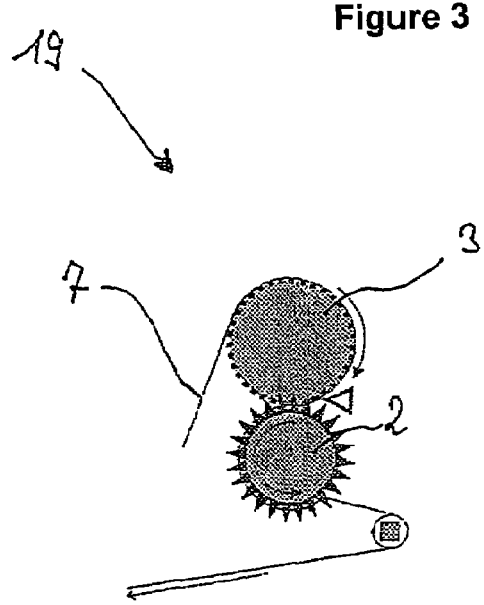
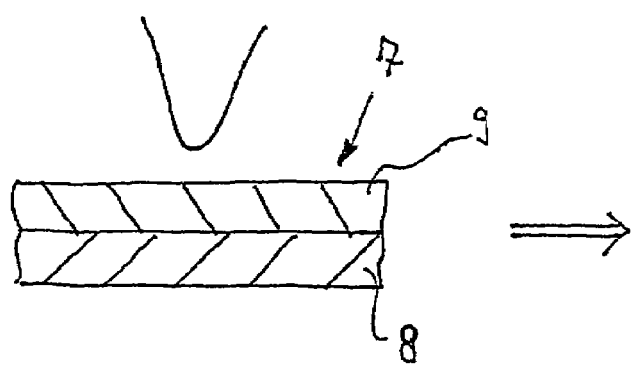
Figure 4
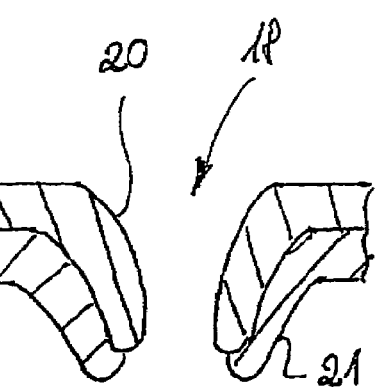
Figure 5

PERFORATED LAMINATE

The present invention relates to a perforated laminate with at least one first and one second layer, as well as a method of production and a product.

A perforated material is disclosed, for example, in EP 0 472 992 B1, which describes a nonwoven having an enlarged surface area with an opening. The opening is produced by means of a roll with a plurality of unheated pins and a roll opposite thereto with a plurality of corresponding openings. The fibers of the nonwoven adjacent to the opening are to be largely unbonded. As a result, the fibers are to remain movable. Consequently, they are also capable of reclosing the opening upon application of a corresponding pressure.

It is therefore an object of the present invention to create a perforated thermoplastic structure of a three-dimensional shape, which possesses a certain insensitivity with respect to its shape.

This object is accomplished by a perforated thermoplastic structure with the features of claim 1. Advantageous further developments are defined in the respectively dependent claims, with further embodiments being described in the following.

The invention comprises a perforated thermoplastic structure with at least a first layer and with a plurality of perforations. The perforations extend through the first layer, with the perforations having a three-dimensional, preferably an approximately conical or cylindrical shape. To the first layer, at least a second layer is joined at least in part. The perforations also extend through the second layer. The second layer forms an inside surface of the shape, whereas the first layer forms an outside surface of the shape. The first layer further comprises a thermoplastic material, whose melting point is lower than the melting point of the thermoplastic material of the second layer.

Preferably, the first layer is molten at least in the region of the perforations, thereby stabilizing the shape. A further development provides that the second layer is at least largely unmolten in the region of the perforation. Another embodiment provides that the second layer is totally unmolten in the region of the perforation.

A permanent deformation of the perforated structure because of a mechanical action for producing the perforated structure therefore occurs only by a corresponding influence of temperature. Preferably, the influence of temperature is simultaneously connected with the transformation process from an imperforate to a perforated structure. This may occur, for example, by means of a calender, which comprises at least a first and a second roll. Preferably, the first roll has a positive structure, which engages in particular a negative structure of the second roll. A transformation process will occur while passing a structure through this calender. When the positive structures, namely the elevations from a surface of the first roll are simultaneously heated, so as to influence the thermoplastic material of the first layer, while the thermoplastic material of the second layer preferably remains largely unaffected, it will be possible to stabilize the shape.

The selection of different melting points of different thermoplastic materials permits allocating different properties to the respective layers. Preferably, the second layer that remains as much as possible unaffected by the energy application during the transformation process, forms in a product at least in part an outside layer. In particular, the melting point of the second layer is selected such that the surface properties in the second layer remain as much as possible unchanged. This is of importance, in particular with respect to using fibers, in particular fibers for nonwovens, for example, not only in the application for hygienic products, but also for industrial products and clothing products. Thus, a solidified material is preferably present in the first layer, whereas the second layer remains unaffected by the application of energy, and thus possesses an unchanged softness. Besides an application of energy during the transformation process, there is also the possibility of carrying out the energy application after the transformation process. This is possible, for example, by means of ultrasound, heat radiation, or also by chemical reactions. The latter occur, for example, by applying a chemical, activating a chemical, or removing a chemical from the first layer, whereby the thermoplastic material of the first layer undergoes at least a partial solidification. To this end, for example, a hardening agent is directly applied to the first layer at least in the region of the perforations, preferably by means of a spraying device. The second layer remains thereby largely unaffected. An application of the agent may occur before or also after the transformation process.

According to a further embodiment, it is also possible to apply an agent between the first and the second layer. During the transformation process, for example, energy is supplied to the structure, which causes the agent to react chemically, for example, in the case of latex, and/or physically, for example, hot melt adhesive. Preferably, the reaction leads to a solidification of the agent itself, which causes the first and the second layer to stabilize. Furthermore, the agent may be of such a nature that it serves as an adhesive. This causes not only the region directly surrounding the perforation to become stabilized, but also the remaining area of the structure.

Examples for advantageous thermoplastic material combinations are shown in the following table:

| Material of the second layer | Material of the first layer |
| --- | --- |
| Spunbonded PP | Spunbonded PE |
| Carded PP | Spunbonded PE |
| Spunbonded PP | Spunbonded BICO, e.g., PP/PE |
| Spunbonded PP | Carded BICO, e.g., PP/PE preferably with PET (for example, between 10% and 40%) |
| PP Film | PE Film |
| Nonwoven PP | PE Film |
| Spunbonded BICO PP/PE | Spunbonded PE |
| Spunbonded BICO PP/PE | PE Film |
| Nonwoven PP | High-bulk nonwoven of BICO PP/PE |
| Spunbonded HDPE | Carded BICO, e.g., PP/PE, preferably with (PET between 10% and 40%) |
| Nonwoven PP | Carded PE |
| Nonwoven PP | PP nonwoven with low melting point, for example Softspun ™ |
| Spunbonded BICO PP/PE | Carded BICO PP/PE |

The weights per unit area were tested as follows:

| Weight per unit area first layer [gsm] | Weight per unit area of second layer [gsm] |
| --- | --- |
| From about 10 to about 50 | From about 10 to about 50 |

Preferably, the first layer has a weight per unit area that is higher than the weight per unit area of the second layer.

The test results were as follows:

| Method | Unit | Sample A | Sample B | Sample C | Sample D | Sample E |
|---|---|---|---|---|---|---|
| Weight per unit area | [g/m²] | 30 | 20 + 30 | 20 + 30 | 26 + 30 | 27 + 30 |
| Tear strength MD | [N/50 mm] | 26.63 | 62.97 | 75.44 | 39.07 | 41.87 |
| Tear strength CD | [N/50 mm] | 23.52 | 24.27 | 29.91 | 17.71 | 10.83 |
| Ratio of tear strengths MD/CD | | 1.13 | 2.60 | 2.52 | 2.21 | 3.87 |
| Elongation at tear MD | [%] | 21.93 | 23.87 | 27.18 | 17.56 | 18.07 |
| Elongation at tear CD | [%] | 30.14 | 39.25 | 41.58 | 78.84 | 75.72 |
| Elongation at 5 N MD | [%] | 2.52 | 1.25 | 1.11 | 1.67 | 1.77 |
| Elongation at 5 N CD | [%] | 7.83 | 9.03 | 7.20 | 22.54 | 35.28 |
| Elongation at 10 N MD | [%] | 5.19 | 2.31 | 2.12 | 3.27 | 3.12 |
| Elongation at 10 N CD | [%] | 12.06 | 14.78 | 12.28 | 38.16 | 62.38 |
| Bond strength | [N/25, 4 mm] | — | 0.160 | 0.173 | 0.037 | 0.031 |
| Denier of second layer | [dtex] | 2.4 | 2.3 | 2.3 | 2.4 | 4.2 |
| Add-On Level Top sheet | [%] | 0.56 | 0.60 | 0.60 | 0.16 | 0.20 |
| Strike-through | [s] | 5.68 | 5.53 | 10.18 | 203.34 | 3.61 |
| Rewet | [g] | 0.109 | 0.098 | 0.113 | 0.105 | 0.105 |
| Ratio of hole diameters MD/CD | | 1.11 | 1.19 | 1.17 | 1.41 | 1.18 |
| Hole surface | [mm²] | 1.28 | 1.30 | 1.29 | 0.90 | 1.11 |
| Open surface (theoretical) | [%] | 19.69 | 19.95 | 19.77 | 13.85 | 17.06 |
| Open surface (measured) | [%] | 18.40 | 18.99 | 17.84 | 15.65 | 17.39 |

Sample A is a PP spunbond and serves as a comparison material. Sample B has a second layer of a spunbond and a first layer of a carded bicomponent material. Sample C has a second layer of a spunbond and a first layer of a carded material. Sample D has a second layer of a bicomponent spunbond and a first layer of a carded bicomponent nonwoven material. Sample E has a second layer of an HDPE spunbond and a first layer of a carded bicomponent material. All samples were each bonded as a single layer before the perforation.

As is shown in particular in the comparison between the measured and the theoretical open surface, and preferably the ratio of the hole sizes MD/CD, it is also possible to stabilize, in particular round apertures of the perforation. The hole diameters range in the MD from 1 to 1.8 mm, and in the CD from 0.8 to 1.7 mm.

A further influence on the hole sizes is exercised by the speed at which the structure advances through the perforation apparatus. The structure advanced through the perforation apparatus at speeds from 5 m/sec. to 130 m/sec. Speeds from 45 m/sec. to 120 m/sec., in particular from 60 m/sc. to 95 m/sec. were found advantageous for producing a stable perforation. In the case of hole diameters in a range below 0.5 mm, it is possible to adjust a higher operating speed. In this instance, it is possible to adjust speeds up to 200 m/sec., preferably speeds above 150 m/sec. The hole diameters will then range from 0.5 to 0.1 mm. Depending on the material, the perforating roll has preferably a temperature from about 100° C. to 160° C. on a groove bottom. During the heating, an oil temperature is adjusted, for example, from 135° C. to 180° C., whereas the opposing roll has preferably a temperature from 45° C. to 95° C., in particular 55° C. to 75° C.

According to a further concept, a perforation apparatus comprises a feed device for a structure that is to be perforated. This feed device is arranged such that the structure advances along the opposing roll at a looping angle above 120°, preferably above 150°, before it is possible to perform a perforation. With that, it is accomplished in particular that in the presence of a heated opposing roll, the structure is supplied to the perforating roll in a preheated state. Moreover, as a result of the looping, a tension decreases in the material that is in contact with the opposing roll, thereby achieving an especially stable perforation.

According to a further embodiment, the opposing roll comprises a coating, preferably a rubber coating. In particular, the coating has a thickness from 1.5 mm to 15 mm, in particular at least 4 mm. The elevations of the perforating roll can engage the coating. Preferably, they engage it up to a depth from about 2.5 to about 6 mm.

According to one embodiment, a two-layered structure that is to be perforated is produced by an integrated production process. For example, in the production of a nonwoven, a spunbonding machine with one or more spin beams is made available. One of the spin beams is used to produce, for example, a polymer blend with a low melting point, and a second spin beam serves to produce a BICO PP/PE nonwoven. Furthermore, it is also possible to apply a second layer to a prefabricated material, and to subsequently perforate the assembly. Furthermore, there is the possibility of producing the first and the second layer inline, and perforating them in a separate process step. As shown by the example of nonwoven fabric, there further exists the possibility of using combinations of film and nonwoven materials. For example, it is possible to extrude a film onto, for example, a carded nonwoven and supply them subsequently to a perforation unit.

When according to an embodiment, a nonwoven material is used as first layer, the fact that nonwoven fibers can be partially premelted will thus make it possible to stabilize the geometry of the shape. In this process, the fibers of the nonwoven may lose, for example, their shape at least in part. According to a further embodiment, the fibers of the nonwoven predominantly retain their shape and become adhesive. According to a further embodiment, the fibers of the first layer are blended at least in part with fibers of a nonwoven material of the second layer, in particular in the form of an entanglement. For example, while two separately produced nonwoven layers may have between them a boundary of materials, the two partially intermixed nonwoven layers exhibit a transition of materials. Beyond the transition of materials, the one and the other layer comprise respectively only one thermoplastic material. Such a structure is produced in particular by means of an inline process. Preferably, the perforated structure comprises a phase transition, or according to a further embodiment, for example, a complete blending of the fibers at least in part in the region of the perforation. Preferably, the first and the second layer are produced in the same manner. Both layers are, for example, extruded nonwovens, which are produced on the same machine. There also is the possibility that different materials with respectively different properties can be combined to one perforated structure. Whereas the one nonwoven comprises at least predominantly PP, the other nonwoven consists for the most part of HDPE or DAPP. Moreover, there exist possibilities of combining different production methods of nonwovens, in particular using high-bulk staple fiber nonwovens with spunbonds or also a melt blown nonwoven with spunbonds, as well as further combinations.

According to a further embodiment, the first layer is bonded to a third layer. The third layer comprises a thermoplastic material, whose melting point is higher than the melting point of the thermoplastic material of the first layer. With that, it is accomplished to produce a type of "sandwich", wherein the intermediate layer provides for the stability of the three-dimensional shape that is present in the three layers.

According to a further concept of the invention, a method is made available for producing a perforated laminate, which comprises at least a first and a second layer. A thermoplastic material of the first layer has a lower melting point than the thermoplastic material of the second layer. The first and the second layer advance together into a perforation calender. In the perforation calender, elevations of a calender roll, preferably at least needlelike projections penetrate the first and the second layer, and the elevations are preferably heated. In this process the second layer comes into contact with the elevations before the first layer.

According to a further development, the second layer is not premelted by its contact with the elevations, whereas the first layer becomes at least in part adhesive.

According to a further method, the second layer is advanced through the calender in an unmelted state, while, however, the first layer melts at least in part. According to a further development, one may also provide that the temperature or the energy application is so high that the thermoplastic material of the first layer loses its original shape at least in part, and solidifies again when being cooled. A corresponding temperature adjustment further makes it possible to premelt the filaments in the first layer, while retaining their filament shape.

Further advantageous features, embodiments, as well as further developments are described in greater detail with reference to the attached drawing. The therein-described features are combinable to further embodiments with the ones described above. In the drawing:

FIG. 3 shows a further perforation apparatus; and

FIGS. 4 and 5 show a basic sequence of a perforation.

Figure 1:
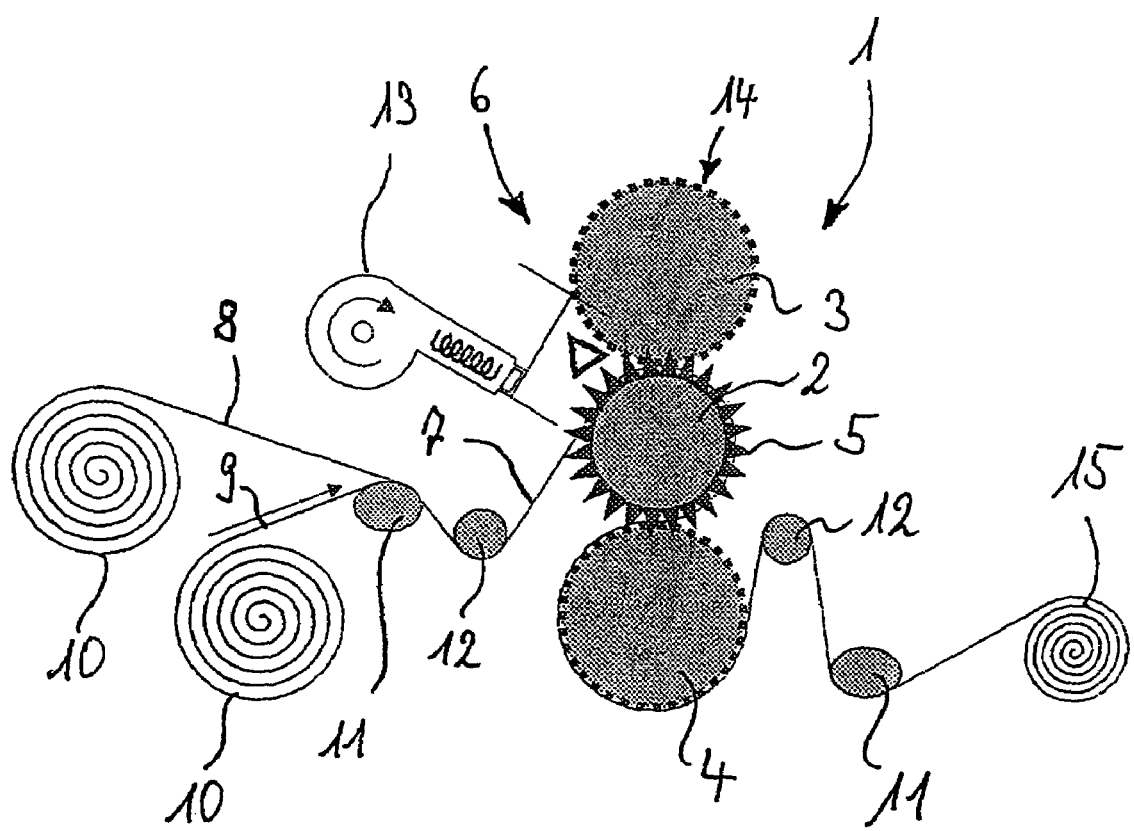
FIG. 1 shows a first perforation apparatus, wherein a structure to be perforated directly advances onto a perforating roll.

FIG. 1 shows a perforation apparatus 1 with a perforating roll 2. Arranged in facing relationship with the perforating roll 2 is an opposing roll 3. In offset relationship thereto, a further, third roll 4 is provided. Elevations 5 that project from the perforating roll 2 engage both the opposing roll 3 and the third roll 4 at least in part. The perforating roll 2, opposing roll 3, and the third roll 4 form a perforation calender 6. A rotational speed of the rolls is adjustable via corresponding gearings or via the control of electric motors. A thermoplastic structure 7 is supplied into the perforation calender 6. The thermoplastic structure is of a flat configuration, which comprises as such a first layer 8 and a second layer 9. Both the first layer 8 and the second layer 9 each advance in this case from an unwinding device 10 to the perforation calender 6. However, before doing so, the first layer 8 and the second layer 9 advance over a spreading roll 11. By combining both layers 8 and 9 by means of the spreading roll 11, it is accomplished that the two layers 8, 9 come to overlie each other totally flat without forming folds. To put the thermoplastic structure 7 under tension, the perforation apparatus 1 of the present embodiment further comprises at least one deflection roll 12. As shown, the deflection roll 12 is independent of the spreading roll 11. However, it is also possible to realize the material tension via a combination of deflection and spreading rolls, in that the first layer 8 and the second layer 9 are guided over the spreading roll 11 directly into the perforation calender 6. In the perforation apparatus 1, the structure 7 is heated at least in part. In this case, the thermal energy is applied to the structure 7 by means of a hot air blower 13. The hot air blower 13 is arranged in the direct vicinity of the perforation calender 6. Preferably, the hot air blower 13 is directly adjacent to the perforating roll 2. A temperature of the heated medium leaving the hot air blower 13 is adapted to the softening point of the thermoplastic material of the first layer. According to one embodiment, the medium is heated at least approximately to this temperature. According to a further development the medium has such a temperature that it heats the first layer to a temperature between the softening point of the thermoplastic material of the first layer and the softening point of the thermoplastic material of the second layer. It is preferred to select such a temperature range for the structure that is to be perforated, also in the case of other methods of applying energy. Decisive in this connection is that temperature, which preserves the thermoplastic material of the first layer. Because of energy losses, for example, from the point of leaving the hot air blower 13 until arriving at the structure 7, and from transferring the energy to the first layer 8, it is possible to adjust the medium to a higher temperature. A corresponding measure also applies, for example, to a heating of the elevations 5 on perforating roll 2 or also to other possibilities of applying energy.

Preferably, the opposing roll 3 shown in FIG. 1 comprises on its surface openings 14 that extend into the opposing roll 3. In their dimensions, the openings 14 approximately correspond to the elevations 5 of the perforating roll 2. The openings 14 may be round holes, elongate holes or, however, also channels, as they result, for example, from the formation of ridges on the surface of the opposing roll 3. As a result of the interaction of the perforating roll 2 and the opposing roll 3, the structure 7 is perforated. The perforated structure 7 advances along the opposing roll 3 to the third roll 4. In so doing, the thermoplastic structure is preferably cooled. As a result of the interaction of the opposing roll 3 and the third roll 4, the perforated thermoplastic structure 7 is deposited on the third roll 4, from which it advances to a deflection roll 12. From the latter, the perforated thermoplastic structure 7 reaches again a spreading roll 11. From the spreading roll 11, the thermoplastic structure 7 advances to a takeup device 15. The winding of the perforated structure 7 occurs under a certain tension, which is adjustable via both the deflection roll 12 and the spreading roll 11. In particular, the tension is adapted as a function of the speed, at which the structure 7 advances to the takeup device 15. The spreading roll 11 prevents folds from forming during the takeup. At the same time, the tension is adjusted so as to avoid that the three-dimensional shape is torn apart and thus destroyed. The thus-produced three-dimensional shape can be wound under higher tensions than a thermoplastic structure 7 that is not fused.

As can be noted from FIG. 1, prefabricated layers are combined and subsequently wound. The bonding of the first layer to the second layer that is accomplished by perforation, will suffice to store the material by means of the takeup device 15 for further processing, without incurring the risk that both layers 8, 9 separate again from each other. According to a further development not shown in greater detail, however, it is also possible to use a structure which is bonded at least in part before and/or after the perforation in a usual manner known from the art.

Figure 2:
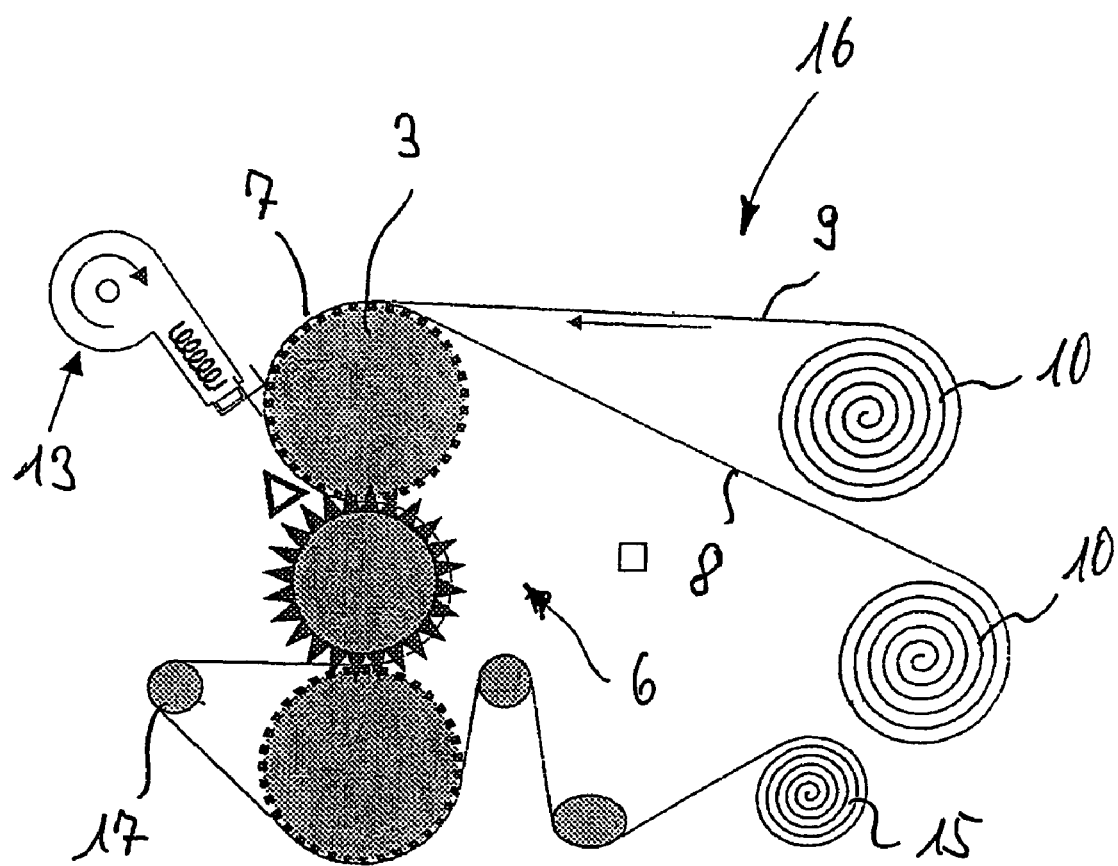
FIG. 2 shows a second perforation apparatus, wherein the structure to be perforated is first supplied to a rotating roll.

FIG. 2 shows a second perforation apparatus 16 similar to FIG. 1, which again comprises a perforation calender 6. Also in this apparatus, a thermoplastic structure 7 advancing from unwinding devices 10 is perforated and wound by means of a takeup device 15. Unlike the first perforation apparatus 1, however, the first layer 8 and the second layer 9 advance in the second perforation apparatus 16 first onto the opposing roll 3, where they are heated by means of the hot air blower 13, and only then to the perforating roll 2. A tension of the material that is to be adjusted in the thermoplastic structure 7 is thus controlled via the rotational speed of the opposing roll 3 and the respective unwinding speed for the first and second layers 8, 9. The passage over the opposing roll 3 makes it further possible that the energy to be applied to the first layer 8 can be applied via the second layer 9, without the first layer 8 having to come into direct contact with the medium. Furthermore, the perforation calender 6 comprises a deflection roll 17 downstream of the perforating roll 2. Preferably, the deflection roll 17 is arranged such that it causes the perforated structure 7 to move under the tension initially away from both the perforating roll 2 and the third roll 4, before advancing again onto the third roll 4. The deflection roll 17 is especially advantageous for material widths of >500 mm. In this connection, one may also supplement the perforation calender 6 with spreading rolls, which are, however, both not shown in greater detail.

The perforation apparatus 1, 16 shown in FIGS. 1 and 2 comprise three rolls, which form the perforation calender 6. The arrangement of the rolls relative to one another is, as shown, such that their centers extend approximately along a straight line. However, the rolls may also be offset from one another, this means at an angle preferably from 160° to 40°. Furthermore, the perforation apparatus 1, 16 may comprise additional devices, such as spraying systems, ultrasonic and measuring devices.

FIG. 3 illustrates a third perforation apparatus 19, in which the perforation calender 6 comprises only an opposing roll 3 and a perforating roll 2. The structure 7 is initially supplied onto the opposing roll 3, and loops about it at an angle, which is, as illustrated, preferably greater than 180°, in particular in a range from 190° to 220°.

FIGS. 4 and 5 are a schematic view of the perforation process of a thermoplastic structure 7 with a first layer 8 and a second layer 9. While the first layer 8 is at least partially premelted at least in the region of the perforation, preferably at least in part fully melted, the second layer 9 retains its shape. This allows to accomplish a stabilization of a three-dimensional shape 18 that is formed by the perforation, with the first layer 8 forming an outer surface 21 of the shape 18, while the second layer 9 forms an inner surface 20 thereof.

Examples for an application of the laminate or structure in a product include hygienic products, sanitary and household products, in particular, wipes, medical products, surface applications in products, filter materials, protective garments, geotextiles, disposable products.

The invention claimed is:

1. A laminate with a perforated thermoplastic structure, said laminate having a machine direction of manufacture (MD) and a cross direction of manufacture (CD), and said product comprising
    a first layer forming an outer surface of the laminate, the first layer comprising a spunbond nonwoven fabric containing filaments of a thermoplastic material,
    a plurality of perforations which extend through the first layer, with the perforations having a three-dimensional shape and a hole diameter in the MD of between 1 and 1.8 mm and in the CD of between 0.8 and 1.7 mm, and
    a second layer comprising a thermoplastic material forming an inner surface of the laminate and at least partially forming a surface of the laminate, the second layer being joined at least partly with the first layer, and also containing the plurality of perforations which extend through the second layer, wherein
    the first and the second layer have fibers which are intermixed at least partially in the region of the perforations,
    portions of the second layer surrounding the three-dimensionally shaped perforations extend into the perforations through the first layer;
    portions of the first and second layers surrounding the three-dimensionally shaped perforations project from the surface of the first layer; and
    the first layer comprises a thermoplastic material whose melting point is lower than the melting point of the thermoplastic material of the second layer and the first layer is at least partly melted in the region of the perforations which stabilizes the structure of the laminate, and the second layer is substantially not melted in the region of the perforations.

2. A laminate according to claim 1, wherein the perforations are of a generally tapered or cylindrical shape.

3. A laminate according to claim 1, wherein the second layer is not melted in any part in the region of the perforations when forming the perforated structure.

* * * * *

UNITED STATES PATENT AND TRADEMARK OFFICE
CERTIFICATE OF CORRECTION

| | | |
|---|---|---|
| PATENT NO. | : 7,390,553 B2 | Page 1 of 1 |
| APPLICATION NO. | : 10/481940 | |
| DATED | : June 24, 2008 | |
| INVENTOR(S) | : Muth et al. | |

It is certified that error appears in the above-identified patent and that said Letters Patent is hereby corrected as shown below:

<u>Column 1,</u>

Line 20, after "claim 1" insert --, by a method of producing a perforated laminate with the steps of claim 7, and by a product of claim 13, and a perforation apparatus with the elements of claim 14 or 15--.

Signed and Sealed this

Eleventh Day of November, 2008

JON W. DUDAS
*Director of the United States Patent and Trademark Office*